(12) United States Patent
Rebec et al.

(10) Patent No.: US 7,896,819 B2
(45) Date of Patent: Mar. 1, 2011

(54) METHOD OF DETERMINING THE CONCENTRATION OF AN ANALYTE IN A BODY FLUID AND SYSTEM IN THEREFOR

(76) Inventors: Mihailo V. Rebec, Bristol, IN (US); James E. Smous, Niles, MI (US); Bryan S. Melle, Elkhart, IN (US); Pamela J. Burson, Bristol, IN (US)

( * ) Notice: Subject to any disclaimer, the term of this patent is extended or adjusted under 35 U.S.C. 154(b) by 20 days.

(21) Appl. No.: 11/665,118

(22) PCT Filed: Oct. 20, 2005

(86) PCT No.: PCT/US2005/037901
§ 371 (c)(1),
(2), (4) Date: Apr. 11, 2007

(87) PCT Pub. No.: WO2006/047290
PCT Pub. Date: May 4, 2006

(65) Prior Publication Data
US 2008/0097240 A1    Apr. 24, 2008

Related U.S. Application Data

(60) Provisional application No. 60/620,835, filed on Oct. 21, 2004.

(51) Int. Cl.
*A61B 5/00* (2006.01)
(52) U.S. Cl. ........................... 600/573; 600/583
(58) Field of Classification Search .................. 600/573, 600/583
See application file for complete search history.

(56) References Cited

U.S. PATENT DOCUMENTS

| | | | |
|---|---|---|---|
| 4,959,305 A * | 9/1990 | Woodrum | 435/7.7 |
| 5,161,532 A | 11/1992 | Joseph | |
| 5,582,184 A | 12/1996 | Erickson et al. | |
| 5,617,973 A | 4/1997 | Seto et al. | |
| 5,682,233 A | 10/1997 | Brinda | |
| 5,746,217 A | 5/1998 | Erickson et al. | |
| 5,780,304 A * | 7/1998 | Matzinger et al. | 436/169 |
| 5,820,570 A | 10/1998 | Erickson et al. | |
| 5,879,310 A | 3/1999 | Sopp et al. | |
| 5,879,311 A | 3/1999 | Duchon et al. | |

(Continued)

FOREIGN PATENT DOCUMENTS

GB          1139891          1/1969

(Continued)

OTHER PUBLICATIONS

Written Opinion corresponding to co-pending International Patent Application Serial No. PCT/US2005/037901, European Patent Office, dated Jun. 22, 2006, 9 pages.

(Continued)

*Primary Examiner* — Max Hindenburg
*Assistant Examiner* — Michael C Stout
(74) *Attorney, Agent, or Firm* — Nixon Peabody LLP (57) ABSTRACT

A method of obtaining a body fluid sample for determining the concentration of an analyte in the body fluid sample comprises applying pressure to the skin of the user. The skin is stretched so as to create a tear in the skin such that the applied pressure causes the body fluid to flow from the tear. The body fluid flowing from the tear is collected. Disclosed is also a pressure member for applying pressure to and stretching skin in preparation for forming a tear in the skin.

26 Claims, 5 Drawing Sheets

U.S. PATENT DOCUMENTS

| | | | |
|---|---|---|---|
| 5,879,367 A | 3/1999 | Latterell et al. | |
| 5,885,211 A * | 3/1999 | Eppstein et al. | 600/309 |
| 5,913,833 A | 6/1999 | Elstrom et al. | |
| 5,964,718 A | 10/1999 | Duchon et al. | |
| 5,972,294 A * | 10/1999 | Smith et al. | 422/58 |
| 6,022,316 A * | 2/2000 | Eppstein et al. | 600/309 |
| 6,027,459 A * | 2/2000 | Shain et al. | 600/573 |
| 6,027,496 A | 2/2000 | Loomis et al. | |
| 6,056,701 A | 5/2000 | Duchon et al. | |
| 6,056,738 A | 5/2000 | Marchitto et al. | |
| 6,066,103 A | 5/2000 | Duchon et al. | |
| 6,080,116 A | 6/2000 | Erickson et al. | |
| 6,080,172 A | 6/2000 | Fujiwara et al. | |
| 6,091,975 A | 7/2000 | Daddona et al. | |
| 6,132,449 A * | 10/2000 | Lum et al. | 606/181 |
| 6,142,939 A | 11/2000 | Eppstein | |
| 6,152,889 A | 11/2000 | Sopp et al. | |
| 6,155,992 A * | 12/2000 | Henning et al. | 600/583 |
| 6,183,434 B1 | 2/2001 | Eppstein | |
| 6,203,504 B1 | 3/2001 | Latterell et al. | |
| 6,283,434 B1 | 9/2001 | Holder | |
| 6,306,152 B1 * | 10/2001 | Verdonk et al. | 606/182 |
| 6,902,905 B2 * | 6/2005 | Burson et al. | 435/14 |
| 2002/0040230 A1 * | 4/2002 | Kuhr et al. | 606/181 |
| 2002/0099308 A1 * | 7/2002 | Bojan et al. | 600/573 |
| 2002/0169394 A1 * | 11/2002 | Eppstein et al. | 600/573 |
| 2003/0143113 A2 * | 7/2003 | Yuzhakov et al. | 422/56 |
| 2003/0191376 A1 | 10/2003 | Samuels et al. | |
| 2003/0200644 A1 * | 10/2003 | Matzinger | 29/592.1 |
| 2004/0236251 A1 * | 11/2004 | Roe et al. | 600/583 |
| 2006/0184189 A1 * | 8/2006 | Olson et al. | 606/181 |

FOREIGN PATENT DOCUMENTS

| | | |
|---|---|---|
| WO | WO 93/17719 | 9/1993 |
| WO | WO 97/07734 | 3/1997 |
| WO | WO 99/44507 | 9/1999 |
| WO | WO 99/44508 | 9/1999 |
| WO | WO 99/44638 | 9/1999 |

OTHER PUBLICATIONS

International Search Report corresponding to co-pending International Patent Application Serial No. PCT/US2005/037901, European Patent Office, dated Jun. 22, 2006, 6 pages.

* cited by examiner

Fig. 8 ated to hold
METHOD OF DETERMINING THE CONCENTRATION OF AN ANALYTE IN A BODY FLUID AND SYSTEM IN THEREFOR

CROSS-REFERENCE TO RELATED APPLICATION

This application claims priority to U.S. Provisional Application No. 60/620,835, filed on Oct. 21, 2004.

FIELD OF THE INVENTION

The present invention relates generally to a method and a system for determining an analyte concentration in a body fluid. More specifically, the invention relates to a method and system for determining an analyte concentration using minimal invasive techniques for reducing the amount of pain to a user.

BACKGROUND OF THE INVENTION

Measuring the analyte concentration in a body fluid is an important procedure for determining the health of a patient and monitoring the progress of an illness or the effectiveness of a treatment. One common procedure is monitoring a patient's blood-glucose concentration level. The traditional glucose-monitoring procedure involves a person lancing a finger to obtain at least 3 microliters (μl) of capillary blood. The capillary blood is then applied to an instrument or analysis device, such as a reagent strip, in which reactions occur. These reactions are usually enzyme mediated and are specific to the analyte of interest. The instrument, which may be a reagent strip, is inserted into a blood-glucose meter for quantification of glucose in the blood sample. The glucose concentration in the blood sample is based on a change in the reflectance of the strip or by the amount of current generated in the instrument.

Traditional glucose monitoring may result in significant discomfort to the individual whose blood is being analyzed due to the volume of blood required for the testing and the site from which a sample is collected. In addition to causing discomfort, the use of needles and lancets typically leaves visible marks at the blood-collection site.

An alternative glucose-monitoring technology known in the art includes providing a significantly less invasive monitoring technique involves the quantification of glucose in interstitial fluid (ISF). This technology allows the gathering of interstitial fluid at an alternate site, such as a forearm of the patient. This is accomplished by creating an aperture of 50 to 400 micrometers (μm) in depth in the epidermis of the patient's skin. This technology involves applying mediation material to the skin surface. The purpose of the mediation material is to convert electromagnetic energy into thermal energy. The depth in which the mediation material penetrates the skin, however, varies between individuals, which affects (a) the efficiency of energy transfer (for forming the aperture), (b) the depth of the formed aperture in the skin, and (c) the pain experienced by the patient. Also, the mediation material may mix with the drawn sample and impact the accuracy of the analysis of the analyte concentration.

This alternative process known in the art usually produces small volumes of fluid that require very refined collection and storage techniques. The process is usually quite painful and may result in long-term scaring. Any loss of sample may result in the need to make a larger aperture, create another aperture, or use more force to obtain a larger sample. Either of these will cause the patient to experience more pain.

Thus, there exists a need for a method and a system for determining an analyte concentration that addresses the above-mentioned problems associated with sample collection and contamination.

SUMMARY OF THE INVENTION

According to one method of obtaining a body fluid sample for determining the concentration of an analyte in the body fluid sample, pressure is applied to the skin of a user. The skin is stretched so as to create a tear in the skin such that the applied pressure causes the body fluid to flow from the tear. The body fluid flowing from the tear is collected.

According to another method of obtaining a body fluid sample for determining the concentration of an analyte in the body fluid sample, pressure is applied to the skin of a user. The skin is stretched and the skin is heated at the site of the pressure to create a tear in the skin such that the pressure causes the body fluid to flow from the tear. The body fluid flowing from the tear is collected.

According to one method of determining an analyte concentration in a body fluid sample, a multilayer film is applied on an area of skin with a cup having a first end adapted to hold the multilayer film. The multilayer film includes a collection layer and a mediation layer including mediation material. The area of the skin is stretched by contacting the area of skin with the first end of the cup. Energy from an electromagnetic source is directed onto the multilayer film such that the mediation material converts the energy from the electromagnetic source to thermal energy to form an aperture in the multilayer film and a tear in the skin. Pressure is applied to the area of the skin surrounding the tear to cause body fluid to flow from the tear and through the aperture to an upper surface of the multilayer film. A volume of the body fluid on the upper surface of the multilayer film is collected while the cup remains in contact with the area of skin.

According to one embodiment, a pressure member for applying pressure to and stretching skin in preparation for forming a tear in the skin and collecting a body fluid sample for analysis of at least one analyte concentration comprises a body formed of resilient material. At least a portion of the body is a film. The film comprises at least a gelatin layer having mediation material.

According to another embodiment, a pressure member for applying pressure to and stretching skin in preparation for forming a tear in the skin and collecting a body fluid sample for analysis of at least one analyte concentration comprises a body formed of resilient material. At least a portion of the body is a multilayer film. The multilayer film comprises at least a collection layer and a mediation layer. The collection layer and the mediation layer are adjacent to each other.

According to a further embodiment, a pressure member for applying pressure to and stretching skin in preparation for forming a tear in the skin and collecting a body fluid sample for analysis of at least one analyte concentration comprises a body and a film. The body is formed of resilient material. The film comprises at least a gelatin layer having mediation material. The film is detachably connected to the body.

According to yet embodiment, a pressure member for applying pressure to and stretching skin in preparation for forming a tear in the skin and collecting a body fluid sample for analysis of at least one analyte concentration comprises a body and a multilayer film. The body is formed of resilient material. The multilayer film comprises at least a collection layer and a mediation layer. The collection layer and the mediation layer are adjacent to each other. The multilayer film is detachably connected to the body.

According to one embodiment, a film for the collection and analysis of a body fluid sample comprises a gelatin layer. The gelatin layer includes mediation material.

According to another embodiment, a multilayer film for the collection and analysis of a body fluid sample comprises a collection layer and a mediation layer. The mediation layer is adjacent to the collection layer.

While the invention is susceptible to various modifications and alternative forms, specific embodiments are shown by way of example in the drawings and are described in detail herein. It should be understood, however, that the invention is not intended to be limited to the particular forms disclosed.

DETAILED DESCRIPTION OF THE ILLUSTRATED EMBODIMENTS

One embodiment of the present invention is directed to a method and a system for creating a tear in the patient's skin for the collection and analysis of body fluid sample from the tear. According to one method, the amount of body fluid sample collected is very small volume. For example, the very small volume of fluid may be less than about 1000 nanoliters (ηl). More typically, the body fluid samples are less than about 500 ηl. The amount of body fluid sample that may be collected may be even as small as 50 or 30 ηl. It is desirable to reduce the collection amount because it reduces the collection time. It is often desirable to collect a small amount of fluid because it may reduce the duration and pain associated with the collection process. The method and system of the present invention combine the functions of collecting a body fluid sample and analyzing these fluids.

Figure 1A:
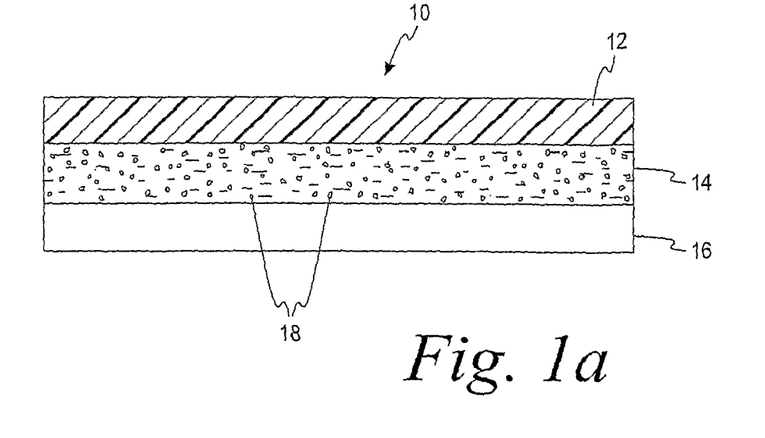
FIG. 1a is an enlarged cross-sectional view of a multilayer film according to one embodiment.

Turning to the drawings and initially to FIG. 1a, to accomplish this combination of functions, a multilayer film 10 is used according to one embodiment. The multilayer film 10 is applied to a test subject's skin and is used to collect a body fluid sample. The process is used to analyze body fluids that are found in the dermis of the skin. Some fluids that may be collected and tested include interstitial fluid (ISF) or a whole blood sample.

According to one embodiment, the multilayer film 10 of FIG. 1a includes a collection layer 12, a mediation layer 14, and a support layer 16. The collection layer 12 is desirably constructed of flexible materials. For example, the collection layer 12 may be made from polymeric materials such as polyethylene or polyvinyl chloride (PVC).

The collection layer 12 of the multilayer film 10 may comprise a reflective material, a reagent, or a combination thereof. In one embodiment, the upper surface (as viewed in FIG. 1a) of the collection layer 12 may be coated with reflective material. Having the collection layer 12 constructed of, or coated with, a reflective material aids in the spectral analysis of light reflected from the collected body fluid sample. The reflective material may be patterned so as to permit the light to reach the mediation layer 14 in some areas, while other areas remain reflective. One non-limited example of a reflective material that may be used in the collection layer 12 is a silver-coated polymer. Another example that may be used in forming the collection layer 12 is a gel material that has a pattern of reflective and non-reflective areas using particles of titanium dioxide suspended therein that would permit electromagnetic energy to reach the mediation layer, if needed.

According to another embodiment, the collection layer 12 may comprise a reagent. The reagent may be deposited on, coated on, or impregnated in the collection layer 12. The optical signature of the collected body fluid sample alone, or the optical signature of a reaction between a reagent and an analyte of interest, is analyzed to determine the analyte concentration in the body fluid sample. It is contemplated that the monitoring may be electrochemical in nature. If the collection layer 12 is designed to be an electrochemical-detection process, electrical leads would likely be extending therefrom. It is also contemplated that the reagents may be patterned in the collection layer so as to perform more than one analysis of the analytes at the same time.

The collection layer 12 generally has a thickness of from about 5 μm to about 500 μm according to one embodiment of the present invention. More specifically, the collection layer 12 typically has a thickness of from about 5 μm to about 100 μm. Depending on the composition of the collection layer, the typically thickness may vary. For example, if the collection layer includes a reflective material, a typically thickness of the collection layer is from about 5 μm to about 10 μm. If the collection layer includes a reagent material, a typically thickness of the collection layer is from about 20 μm to about 100 μm.

The multilayer film 10 is shown in FIG. 1a also includes the mediation layer 14. In forming the multilayer film 10, the mediation layer 14 according to one embodiment may coat the collection layer 12. It is contemplated that the mediation layer 14 may be applied to the collection layer 12 by methods other than coating. For example, the mediation layer 14 may be applied to the collection layer 12 by a sputter-deposition process.

The thickness of the mediation layer 14 may vary according to the amount of thermal energy applied to the multilayer film 10 for creating the tear in the patient's skin, and collecting a sample as is described in detail below. According to one embodiment of the present invention, the thickness of the mediation layer 14 is from about 15 μm to about 50 μm. More specifically, the thickness of the mediation layer 14 is typically from about 20 μm to about 35 μm.

According to one embodiment, the mediation layer 14 includes gelatin and a mediation material 18 suspended therein. In one embodiment, the mediation material 18 is carbon black. The mediation material may be made of electromagnetic-energy absorbent materials. Another example of a mediation material is a dye. To aid in suspending the mediation material 18, the gelatin may include surfactants according to one embodiment. The addition of the surfactants to the mediation layer 14 also results in forming gelatin having hydrophobic characteristics such the gelatin does not absorb water from a very small sample. Surfactants allow body fluids to flow and pool, which assists in collection of the body fluid sample.

The support layer 16 of the multilayer film 10 is desirably constructed of flexible materials. For example, the support layer 16 may be made from polymeric materials such as polyethylene or polyvinyl chloride (PVC). The support layer may be made of other materials such as cellulose. It is contemplated that the materials in forming the support layer 16 may include additives. Desirable additives includes those that enhance one or more of the following: (a) support strength, (b) the ability of the support layer material to stretch, and (c) the ability to control fluid flow. The support layer 16 generally has a thickness of from about 15 µm to about 100 µm according to one embodiment. More specifically, the support layer 16 typically has a thickness of from about 15 µm to about 30 µm.

It is contemplated that other films may be used other than the above-described multilayer film 10. For example, referring to FIG. 1b, a multilayer film 110 comprises the collection layer 12 and mediation layer 14. According to a further embodiment, a film 210 of FIG. 1c may include a mediation layer 214. The mediation layer 214 is formed from gelatin and includes a mediation material 218 therein. The mediation layer 214 may include a reflective material, a reagent or a combination thereof as described above with respect to the collection layer 12.

Figure 1B:
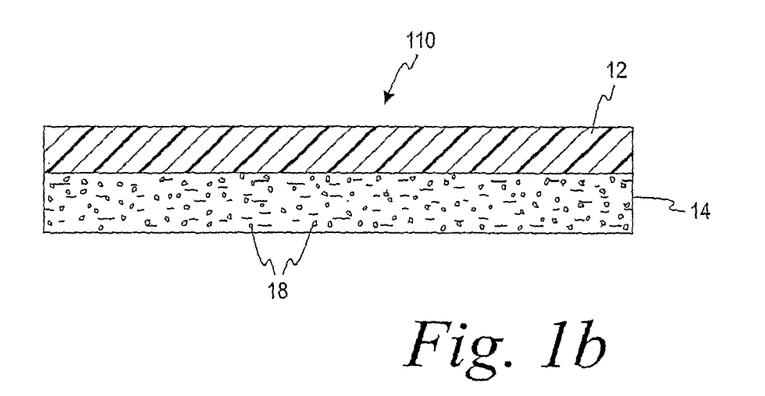
FIG. 1b is an enlarged cross-sectional view of a multilayer film according to another embodiment.
Figure 1C:
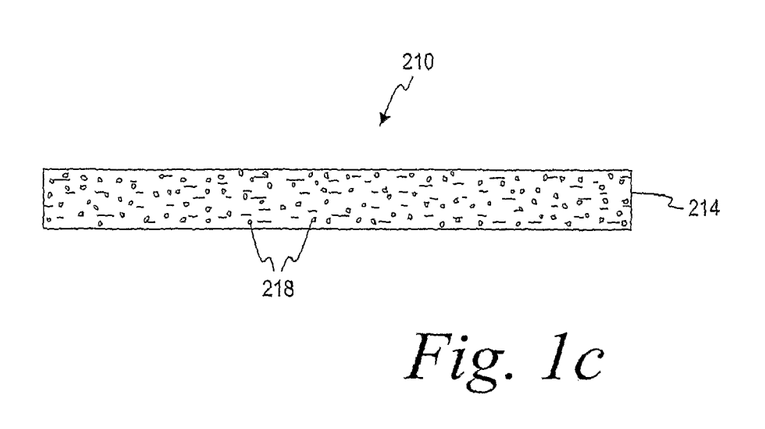
FIG. 1c is an enlarged cross-sectional view of a multilayer film according to a further embodiment.

The films 10, 110, 210 according to one embodiment are used to collect and analyze up to about 1000 ηl of body fluid and desirably sample sizes of less than about 500 ηl to determine the concentration of one or more analytes in the body fluid sample. The amount of body fluid sample that may be collected may be even as small as 50 or 30 ηl. One specific example that may be determined is the amount of glucose in interstitial fluid.

Figure 2:
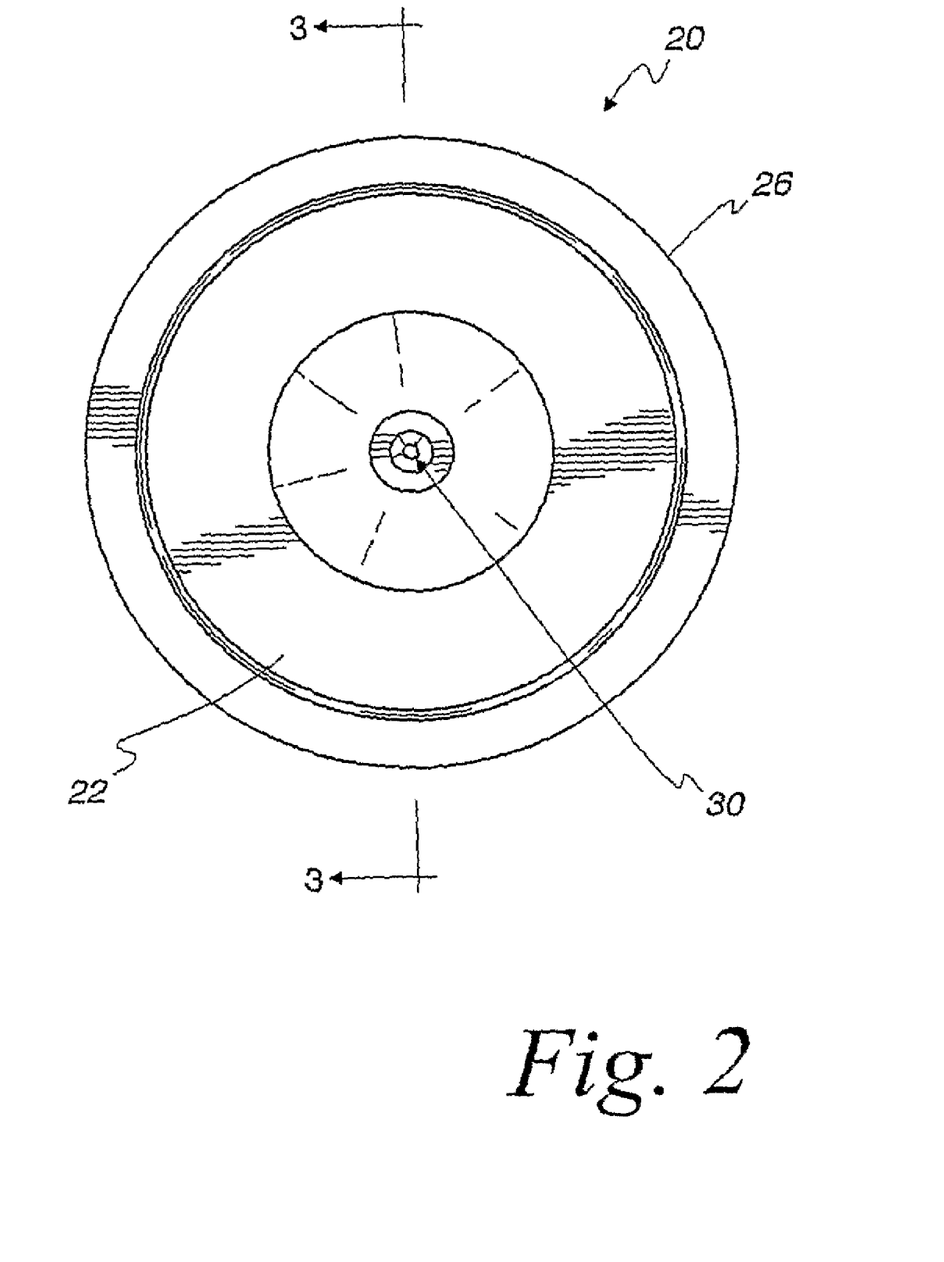
FIG. 2 is a top view of the interior of a cup for use with the multilayer film of FIG. 1a according to one embodiment of the present invention.
Figure 3:
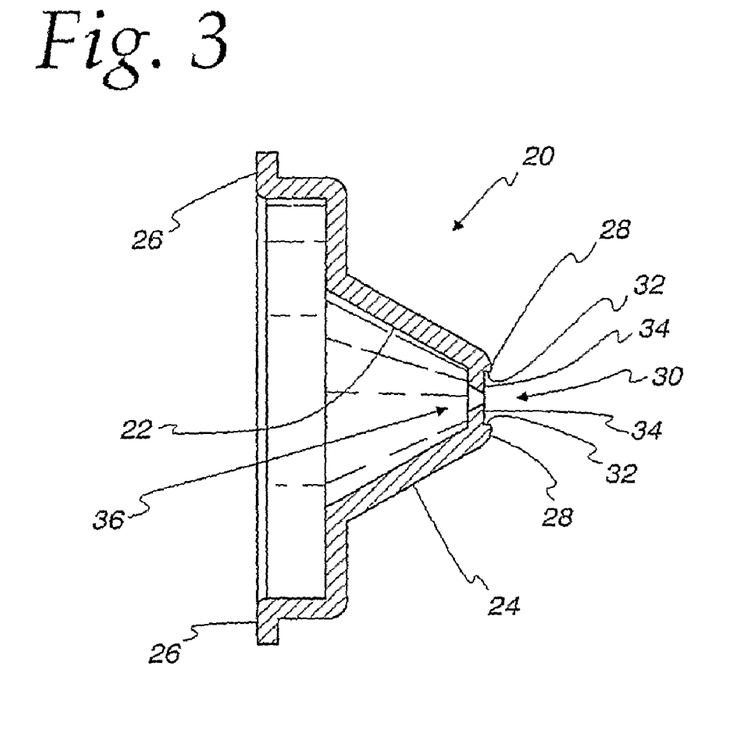
FIG. 3 is a cross-sectional view of the cup taken generally along line 3-3 of FIG. 2.

Turning to FIGS. 2 and 3, a collection cup 20 for use with the film (e.g., multilayer film 10) for collecting and analyzing a body fluid sample is shown according to one embodiment of the present invention. The cup 20 will be described with respect to the multilayer film 10, although it is contemplated that other films such as films 110 and 210 may be used with the cup.

Generally, as is described in detail below, the collection cup 20 is used to collect the body fluid sample as well as to hold the sample for analysis. The cup 20 also holds the multilayer film 10 that is used in the collection and analysis of the sample and applies a pressure to a patient's skin. The collection cup 20 includes an interior surface 22, an exterior surface 24, a bottom rim 26, and a top or apex 28. The top 28 includes a recess 30 that is bounded by a sidewall 32 and a bottom surface 34. The bottom surface 34 of FIG. 3 is shown as being substantially flat. The top 28 also forms an aperture 36 that extends from the interior of the cup 20 through a recess 30 to the exterior of the cup 20. The cup 20 may be constructed of a flexible, elastic material such as, for example, rubber, polycarbonate or other suitable polymers generally used to form molded-polymeric parts.

Figure 4:
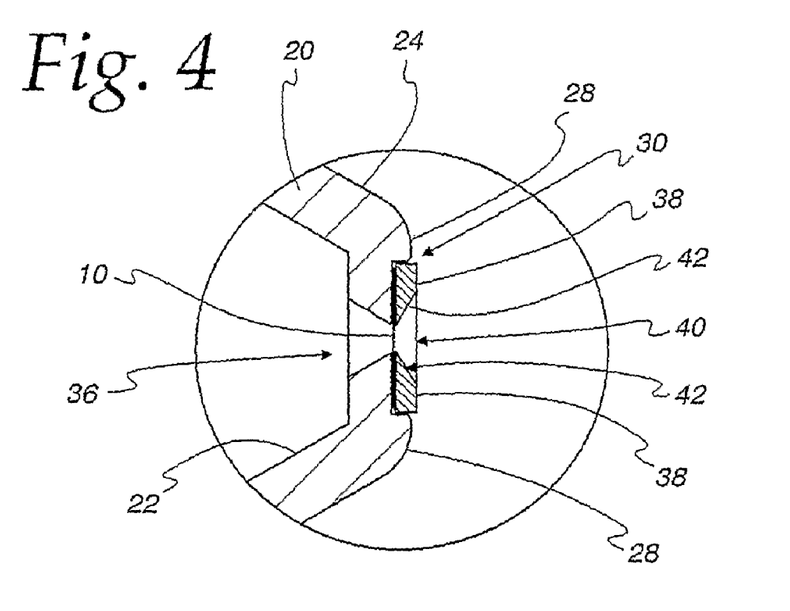
FIG. 4 is an enlarged cross-sectional view of a portion of the cup of FIG. 2 including the multilayer film of FIG. 1.

Referring also to FIG. 4, there is shown an enlarged view of the top 28 of the cup 20. The multilayer film 10 is disposed in the recess 30 such that the support layer 16 of the multilayer film 10 contacts the bottom surface 34. The multilayer film 10 is disposed over the aperture 36 that is disposed in the recess 30, and frictionally held in position by an insert 38. The insert 38 is designed to fit in the recess 30, and has a shape substantially matching that of the recess 30. The insert 38 presses against the sidewall 32 of the recess to hold the multilayer film 10 against the bottom surface 34. The insert 38 forms an aperture 40 that has a center substantially aligned with a center of the aperture 36 in the recess 30. The aperture 40 defines an interior surface 42 of the insert 38.

Figure 5:
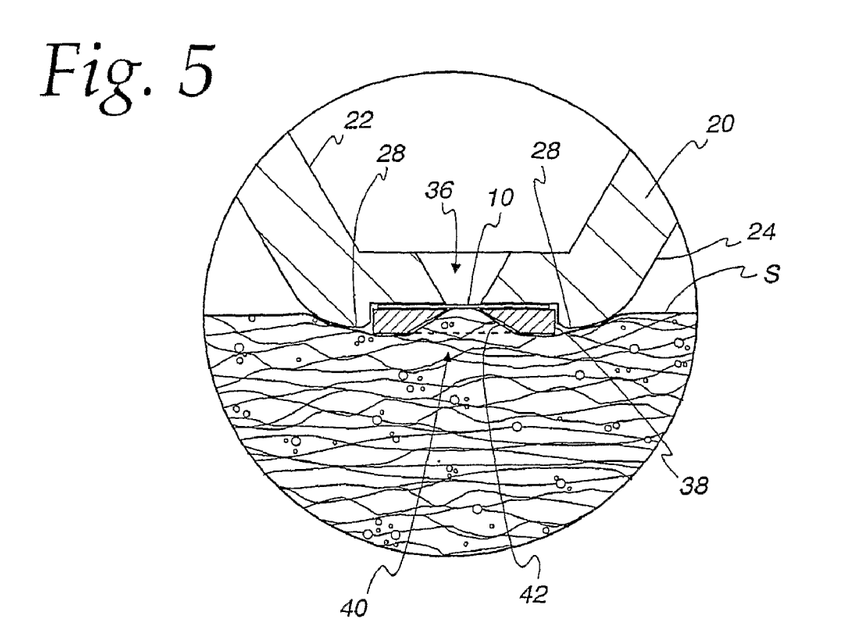
FIG. 5 is an enlarged cross-sectional view of a portion of the cup of FIG. 2 including the multilayer film of FIG. 1a in contact with a patient's skin according to one embodiment.

Referring also to FIG. 5, the top 28 of the cup 20 is shown pressed into a patient's skin S. Generally, in use, the top 28 of the cup 20 is brought into contact with a small area of a patient's skin S, such as a forearm or other area of skin S. Pressure is applied to the rim 26 of the cup 20. The top 28 presses against the patient's skin S to deform the skin S causing the skin S to stretch and, consequently, thin out. A force of from about three to about five pounds is applied to the cup 20 according to one embodiment. This action, in turn, delivers a pressure of from about three to about five pounds to the patient's skin thereby stretching the skin and creating an upward pressure on the skin. While the skin S is in contact with the top 28 that is being pressed downward (as viewed in FIG. 5), the area of skin S bound by the interior surface 42 of the insert 38 is pushed upward. The interior surface 42 is pushed upward because the fluids, including the ISF located in the dermis, under that area of skin are forced upward against the dermis of the skin as the adjacent areas are downwardly forced by the top 28 of the cup 20. The upwardly pushed area of skin S bound by the interior surface 42 of the insert 38 contacts the interior surface 42 and is pressed against the support layer 16 of the multilayer film 10 held by the cup 20. Due to the elastic nature of the multilayer film 10, the film 10 deforms slightly as the skin S presses against it.

It is contemplated that other pressure members may be used other than the above-described cup 20. Desirable pressure members would need to apply pressure and stretch the skin in preparation for forming a tear in the skin and collecting a body fluid sample. For example, pressure members such as metal rings may be designed to deliver pressure to the skin and stretch the skin in a similar manner. Another contemplated example would be a process in which the skin is picked-up and pinched within a fixture.

According to one embodiment, the pressure member comprises a body formed of resilient material. According to this embodiment, at least a portion of the body is a film. In such an embodiment, the body and the film are integrated with each other. The film may comprise one layer such as a gelatin layer having mediation material. It is contemplated, however, that the body may include a multilayer film such as described above with multilayer films 10, 110. According to another embodiment, the body and the film may be separate components that are detachably connected. The film in this embodiment may also comprise one layer such as a gelatin layer having mediation material or may be a multilayer film such as described above with multilayer films 10, 110.

Thus far, methods have been described in connection with applying a positive pressure to press the skin S against the multilayer film (e.g., pressing the cup 20 against the skin S). In alternative embodiments, however, negative pressure may also be used. For example, a vacuum may be used to pull the skin S against the film such as multilayer film 10.

According to one method, a body fluid sample is obtained to determine an analyte concentration of an analyte thereof. Pressure is applied to the skin of a user and the skin is stretched so as to create a tear in the skin such that the applied pressure causes the body fluid to flow from the tear. The body fluid flowing from the tear is collected. The analyte concentration is typically analyzed to determine the analyte concentration in the body fluid sample by, for example, optical processes. The applied pressure and stretching may be applied by a pressure member such as, for example, cup 20. The applied pressure according to one method is a positive pressure. It is contemplated, as discussed above, that the applied pressure may be a negative pressure.

Figure 6:
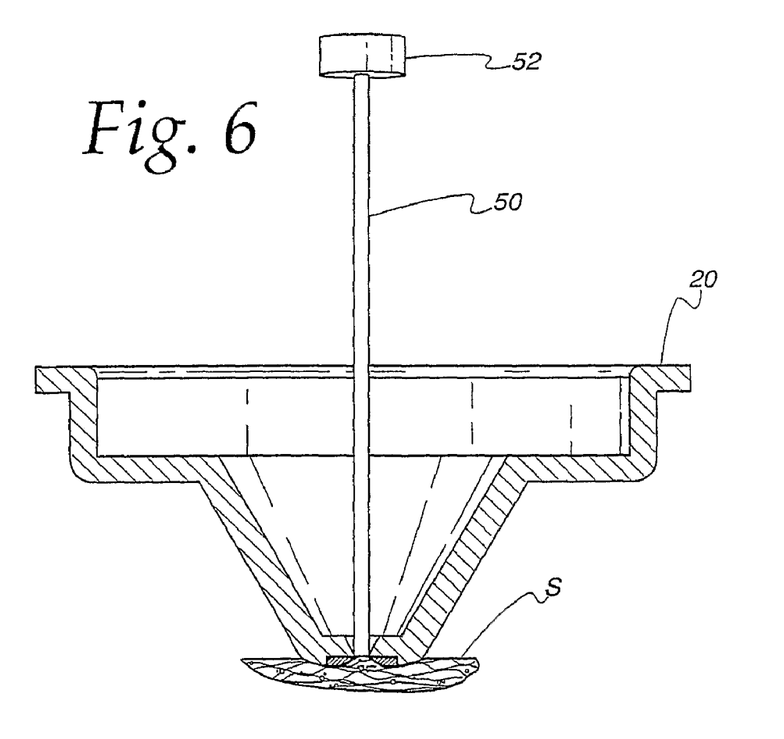
FIG. 6 is a diagram of a system for determining an analyte concentration in a body fluid sample according to one embodiment.

Referring now to FIG. 6, the stratum corneum of the skin S may be softened according to one method. For example, the skin S may be softened by using one of several heating methods, such as an electromagnetic-radiation source, a hot wire, or heated air. In one embodiment, energy in the form of a laser beam 50 emitted from a light source 52 such as a laser diode, for example, is directed onto at least a portion of the multilayer film 10. It is contemplated that other films such as films 110 and 210 may be used in conjunction with one of the several heating methods.

According to one embodiment, the light source provides a 870 nanometer (nm) pulsed-laser beam released at a power of from about 300 to about 450 milliwatts for a duration of from about 120 milliseconds to about 300 milliseconds. According to one embodiment, the laser beam 50 has a diameter of from about 50 μm to about 500 μm. The electromagnetic radiation from the laser beam 50 is absorbed by the mediation material 18 in the mediation layer 14 of the multilayer film 10, and converted into thermal energy. The thermal energy is transferred to the stratum corneum of the skin S. This heating process softens and weakens the stratum corneum, and disrupts the junction between the dermis and the epidermis. The epidermis layer of the skin S is stretched, causing it to rupture and tear. The at least one tear is created by the stretching of the epidermis by the cup, and by the disruption of the junction between the dermis and the epidermis caused by the thermal energy.

Figure 7:
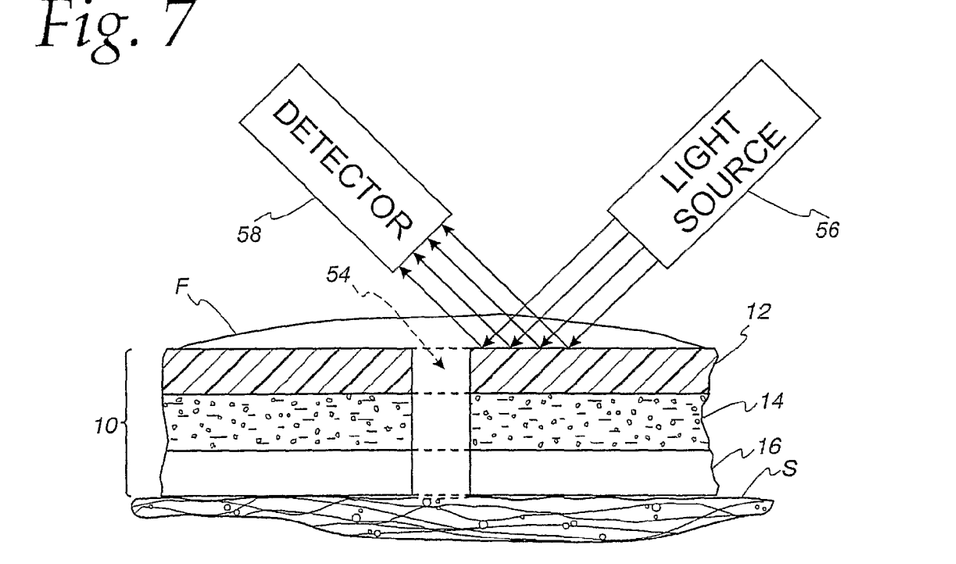
FIG. 7 is an enlarged view of the multilayer film of FIG. 1a pressed against a patient's skin using the system of FIG. 6.

Referring also to FIG. 7, on creation of a tear in the patient's epidermis, the body fluid that is under pressure in the dermis—caused by application of the cup 20—flows through the tear in the epidermis, and through the aperture 54 formed in the multilayer film 10 by the laser beam 50. Histological evaluation of the skin points to a rapid repair of the skin tear unlike the long lasting damage that is observed after standard skin-ablation techniques. Thus, the resultant tear produces no lasting evidence from the ablation on the skin.

The sample is obtained from the upper layer of the dermis, which is most closely associated with the capillary plexus region. This region has good interstitial fluid/capillary blood exchange. The body fluid(s) F flowing through the aperture 54 pools on the top of the multilayer film 10. The positive pressure of interstitial fluid contributes to forming the tear in the epidermis, and the forces of pressure and stretching provided by the cup 20 allow less force to be required from a single component thereby reducing the perceived pain felt by the person being sampled.

The sample fluid F pools on the upper surface (as viewed in FIG. 7) of the collection layer 12 of the multilayer film 10. After a sufficient sample fluid F volume has pooled, the sample fluid F is illuminated with light from a light source 56 according to one method. Non-limiting examples of light sources include monochromatic light, polychromatic light and infrared light. It is contemplated that other focused light sources may be employed. One or more detectors 58 collects light reflected from the sample fluid F. It is also contemplated that depending on the type of skin, the pressure of the cup alone may create sufficient sample fluid F without the need for a light source.

The at least one detector 58 may comprise, for example, a silicon detector. Alternatively, the at least one detector 58 may comprise a fiber-optic bundle that pipes the collected reflected light back to a detector or spectrometer. One non-limiting example of a detector is an extended InGaAs detector. It is contemplated that other detectors may be employed. The detector outputs a signal indicative of the collected reflected light to a system (not shown) for evaluating the collected reflected light. The system has one or more embedded algorithms that are applied to the spectral data to translate the data to the concentration values of the one or more analytes of interest.

To aid in the collection of light reflected from the sample, the upper surface (as viewed in FIG. 7) of the collection layer 12 of the multilayer film 10 may comprise a reflective surface (e.g., a silver coating). In yet another alternative embodiment, the collection layer 12 includes a reagent that reacts with the analyte of interest to develop an optical signature related to the analyte of interest.

Figure 8:
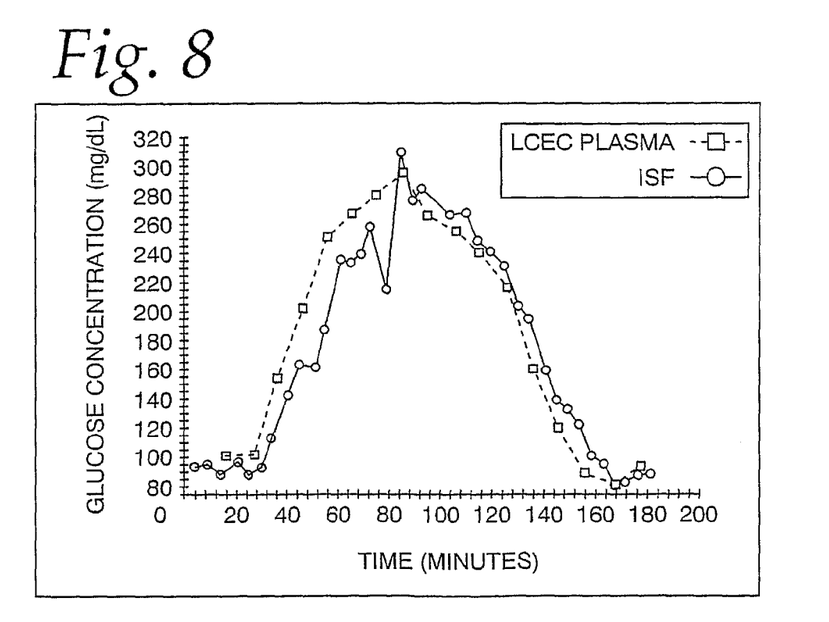
FIG. 8 is a graph illustrating data from an analysis of a glucose tolerance study using the method and system of the present invention.

A study was performed to determine the accuracy of the method and system. An electrochemical amperometric glucose analysis was conducted and the results are graphically illustrated in FIG. 8. The study was a glucose intolerance study used to study the relationship between ISF glucose and plasma glucose under rapidly changing glucose concentration conditions. The graph in FIG. 8 illustrates ISF and plasma glucose concentrations versus time. The close tracking of the connecting lines in FIG. 8 illustrates that there are not significant variations between the samplings.

Process A

A method of obtaining a body fluid sample for determining the concentration of an analyte in the body fluid sample, the method comprising the acts of:

applying pressure to the skin of a user;

stretching the skin so as to create a tear in the skin such that the applied pressure causes the body fluid to flow from the tear; and collecting the body fluid flowing from the tear.

Process B

The method of process A further comprising analyzing the analyte concentration in the body fluid sample.

Process C

The method of process B wherein the analyzing is performed optically.

Process D

The method of process A wherein applying pressure and stretching comprises pressing a cup against the skin to create pressure on the skin, the cup includes a skin-contacting area, the skin-contacting area forms an aperture therethrough in which the body fluid sample is collected.

Process E

The method of process A wherein the body fluid sample is interstitial fluid.

Process F

The method of process A wherein the applied pressure is a positive pressure.

Process G

The method of process A wherein the applied pressure is a negative pressure.

Process H

A method of obtaining a body fluid sample for determining the concentration of an analyte in the body fluid sample, the method comprising the acts of:

applying pressure to the skin of a user;

stretching the skin;

heating the skin at the site of the pressure to create a tear in the skin such that the pressure causes the body fluid to flow from the tear; and collecting the body fluid flowing from the tear.

Process I
The method of process H further comprising analyzing the analyte concentration in the body fluid sample.

Process J
The method of process I wherein the analyzing is performed optically.

Process K
The method of process H wherein applying pressure and stretching comprises pressing a cup against the skin to create pressure on the skin, the cup includes a skin-contacting area, the skin-contacting area forms an aperture therethrough in which the body fluid sample is collected.

Process L
The method of process K wherein heating the skin comprises applying a film to the skin, the film includes a mediation layer, and pressing the film against the skin with the skin-contacting area of the cup, and further comprising directing electromagnetic radiation onto at least a portion of the film to form an aperture in the film and a tear in skin.

Process M
The method of process L wherein the mediation layer includes gelatin and mediation material, the mediation material is located within the gelatin.

Process N
The method of process K wherein heating the skin comprises applying a multilayer film to the skin, the multilayer film includes a collection layer and a mediation layer, the collection layer and the mediation layer are adjacent to each other, and pressing the multilayer film against the skin with the skin-contacting area of the cup, and further comprising directing electromagnetic radiation onto at least a portion of the multilayer film to form an aperture in the multilayer film and a tear in skin.

Process O
The method of process N wherein the mediation layer includes gelatin and mediation material, the mediation material is located within the gelatin.

Process P
The method of process N wherein directing electromagnetic radiation comprises directing electromagnetic radiation via a laser onto at least a portion of the multilayer film.

Process Q
The method of process K wherein heating the skin comprises applying a multilayer film to the skin, the multilayer film includes a collection layer, a gelatin layer having a mediation material, and a support layer, the gelatin layer being located between the collection and the support layers, and pressing the multilayer film against the skin with the skin-contacting area of the cup, and further comprising directing electromagnetic radiation onto at least a portion of the multilayer film to form an aperture in the multilayer film and a tear in skin.

Process R
The method of process H wherein heating the skin comprises directing electromagnetic radiation from a laser.

Process S
The method of process H wherein the body fluid is interstitial fluid.

Process T
The method of process H wherein the applied pressure is a positive pressure.

Process U
The method of process H wherein the applied pressure is a negative pressure.

Process V
A method for use in determining an analyte concentration in a body fluid sample, the method comprising the acts of:
applying a multilayer film on an area of skin with a cup having a first end adapted to hold the multilayer film, the multilayer film including a collection layer and a mediation layer including mediation material;
stretching the area of the skin by contacting the area of skin with the first end of the cup;
directing energy from an electromagnetic source onto the multilayer film such that the mediation material converts the energy from the electromagnetic source to thermal energy to form an aperture in the multilayer film and a tear in the skin;
applying pressure to the area of the skin surrounding the tear to cause body fluid to flow from the tear and through the aperture to an upper surface of the multilayer film; and
collecting a volume of the body fluid on the upper surface of the multilayer film while the cup remains in contact with the area of skin.

Process W
The method of process V further comprising providing a reagent in the multilayer film for reacting with the analyte in the body fluid sample.

Process X
The method of process V further comprising conducting a spectral analysis of the collected body fluid sample while the cup remains in contact with the skin.

Process Y
The method of process X wherein conducting a spectral analysis comprises illuminating the collected body fluid sample.

Process Z
The method of process Y wherein illuminating comprises illuminating the body fluid sample with monochromatic light.

Process AA
The method of process Y wherein illuminating comprises illuminating the body fluid sample with polychromatic light.

Process BB
The method of process Y wherein illuminating comprises illuminating the body fluid sample with infrared light.

Process CC
The method of process Y wherein conducting a spectral analysis further comprises detecting light reflected from the body fluid sample.

Process DD
The method of process CC wherein the upper surface of the multilayer film on which the body fluid sample is collected includes a reflective material.

Process EE
The method of process V wherein the mediation material is carbon black.

Process FF
The method of process V wherein the body fluid is interstitial fluid.

Process GG
The method of process V wherein the multilayer film further includes a support layer, the mediation layer being located between the collection and the support layers.

Process HH
The method of process V wherein the mediation layer includes gelatin and the mediation material.

Process II
The method of process V wherein the electromagnetic source is a laser.

Embodiment JJ

A pressure member for applying pressure to and stretching skin in preparation for forming a tear in the skin and collecting a body fluid sample for analysis of at least one analyte concentration, the pressure member comprising a body formed of resilient material, at least a portion of the body being a film, the film comprising at least a gelatin layer having mediation material.

Embodiment KK

The pressure member of embodiment JJ wherein the mediation material is a high electromagnetic energy absorbent material.

Embodiment LL

The pressure member of embodiment KK wherein the mediation material is carbon black.

Embodiment MM

The pressure member of embodiment JJ wherein the gelatin layer further includes reflective material.

Embodiment NN

The pressure member of embodiment JJ wherein the gelatin layer further includes a reagent.

Embodiment OO

The pressure member of embodiment JJ wherein the body comprises a generally conical-shaped cup having an open end that is adapted to press against the skin.

Embodiment PP

A pressure member for applying pressure to and stretching skin in preparation for forming a tear in the skin and collecting a body fluid sample for analysis of at least one analyte concentration, the pressure member comprising a body formed of resilient material, at least a portion of the body being a multilayer film, the multilayer film comprising at least a collection layer and a mediation layer, the collection layer and the mediation layer being adjacent to each other.

Embodiment QQ

The pressure member of embodiment PP wherein the mediation layer includes gelatin and mediation material.

Embodiment RR

The pressure member of embodiment PP wherein the mediation material is a high electromagnetic energy absorbent material.

Embodiment SS

The pressure member of embodiment RR wherein the mediation material is carbon black.

Embodiment TT

The pressure member of embodiment PP wherein the multilayer film further comprises a support layer, the mediation layer being located between the collection and the support layers.

Embodiment UU

The pressure member of embodiment PP wherein the collection layer includes reflective material.

Embodiment VV

The pressure member of embodiment PP wherein the collection layer includes a reagent.

Embodiment WW

The pressure member of embodiment PP wherein the body comprises a generally conical-shaped cup having an open end that is adapted to press against the skin.

Embodiment XX

A pressure member for applying pressure to and stretching skin in preparation for forming a tear in the skin and collecting a body fluid sample for analysis of at least one analyte concentration, the pressure member comprising a body and a film, the body being formed of resilient material, the film comprising at least a gelatin layer having mediation material, the film being detachably connected to the body.

Embodiment YY

The pressure member of embodiment XX wherein the mediation material is a high electromagnetic energy absorbent material.

Embodiment ZZ

The pressure member of embodiment YY wherein the mediation material is carbon black.

Embodiment AAA

The pressure member of embodiment XX wherein the gelatin layer further includes reflective material.

Embodiment BBB

The pressure member of embodiment XX wherein the gelatin layer further includes a reagent.

Embodiment CCC

The pressure member of embodiment XX wherein the body comprises a generally conical-shaped cup having an open end that is adapted to press against the skin.

Embodiment DDD

A pressure member for applying pressure to and stretching skin in preparation for forming a tear in the skin and collecting a body fluid sample for analysis of at least one analyte concentration, the pressure member comprising a body and a multilayer film, the body being formed of resilient material, the multilayer film comprising at least a collection layer and a mediation layer, the collection layer and the mediation layer being adjacent to each other, the multilayer film being detachably connected to the body.

Embodiment EEE

The pressure member of embodiment DDD wherein the mediation layer includes gelatin and mediation material.

Embodiment FFF

The pressure member of embodiment DDD wherein the mediation material is a high electromagnetic energy absorbent material.

Embodiment GGG

The pressure member of embodiment FFF wherein the mediation material is carbon black.

Embodiment HHH

The pressure member of embodiment DDD wherein the multilayer film further comprises a support layer, the mediation layer being located between the collection and the support layers.

Embodiment III

The pressure member of embodiment DDD wherein the collection layer includes reflective material.

Embodiment JJJ

The pressure member of embodiment DDD wherein the collection layer includes a reagent.

Embodiment KKK

The pressure member of embodiment DDD wherein the body comprises a generally conical-shaped cup having an open end that is adapted to press against the skin.

Embodiment LLL

A film for the collection and analysis of a body fluid sample, the film comprising a gelatin layer, the gelatin layer including mediation material.

Embodiment MMM

The film of embodiment LLL wherein the mediation material is a high electromagnetic energy absorbent material.

Embodiment NNN

The film of embodiment MMM wherein the mediation material is carbon black.

Embodiment OOO

The film of embodiment LLL wherein the gelatin layer further includes reflective material.

Embodiment PPP

The film of embodiment LLL wherein the gelatin layer further includes a reagent.

Embodiment QQQ

A multilayer film for the collection and analysis of a body fluid sample, the multilayer film comprising a collection layer and a mediation layer, the mediation layer being adjacent to the collection layer.

Embodiment RRR

The multilayer film of embodiment QQQ wherein the mediation layer comprises gelatin and mediation material.

Embodiment SSS

The multilayer film of embodiment QQQ wherein the mediation material is a high electromagnetic energy absorbent material.

Embodiment TTT

The multilayer film of embodiment SSS wherein the mediation material is carbon black.

Embodiment UUU

The multilayer film of embodiment QQQ further comprising a support layer, the mediation layer being located between the collection and support layers.

Embodiment VVV

The multilayer film of embodiment QQQ wherein the collection layer includes reflective material.

Embodiment WWW

The pressure member of embodiment QQQ wherein the collection layer includes a reagent.

The invention claimed is:
1. A method of obtaining a body fluid sample for determining the concentration of an analyte in the body fluid sample, the method comprising the acts of:
 applying pressure to skin of a user with a pressure member, the pressure member including a film;
 directing electromagnetic radiation onto at least a portion of the film to heat the skin of the user at a site of the pressure, which softens the skin of the user at the site of the pressure;
 stretching the skin by use of the applied pressure member, the stretching creating a tear in the skin such that the applied pressure causes the body fluid sample to flow from the tear.
2. The method of claim 1, further comprising collecting the body fluid sample flowing from the tear.
3. The method of claim 2, wherein the pressure member includes a skin-contacting area, the skin-contacting area forming an aperture therethrough.
4. The method of claim 1, wherein the body fluid sample is interstitial fluid.
5. The method of claim 3, further comprising the act of applying a film to the skin, the film including a mediation layer, and further comprising the acts of pressing the film against the skin with the skin-contacting area of the pressure member, and directing electromagnetic radiation onto at least a portion of the film to form an aperture in the film and to assist in creating the tear in the skin.

6. The method of claim 4, wherein the mediation layer includes gelatin and mediation material, the mediation material being located within the gelatin.

7. The method of claim 3, further comprising the act of applying a multilayer film to the skin, the multilayer film including a collection layer and a mediation layer, the collection layer and the mediation layer being adjacent to each other, further comprising the acts of pressing the multilayer film against the skin with the skin-contacting area of the pressure member, and directing electromagnetic radiation onto at least a portion of the multilayer film to form an aperture in the multilayer film and to assist in creating the tear in the skin.

8. The method of claim 3, further comprising the acts of applying a multilayer film to the skin, the multilayer film includes a collection layer, a gelatin layer having a mediation material, and a support layer, the gelatin layer being located between the collection and the support layers, and pressing the multilayer film against the skin with the skin-contacting area of the pressure member, and further comprising the act of directing electromagnetic radiation onto at least a portion of the multilayer film to form an aperture in the multilayer film and to assist in creating the tear in the skin.

9. The method of claim 5, wherein the pressure member has a first end adapted to hold the film, the mediation layer including mediation material;
wherein the stretching of the skin comprises contacting the skin with the first end of the pressure member;
wherein the directing of electromagnetic radiation causes the mediation material to convert the radiation to thermal energy to form the aperture in the film and the tear in the skin;
wherein the applying of pressure to the skin causes body fluid to flow from the tear and through the aperture in the skin-contacting area of the pressure member to an upper surface of the film; and
further including collecting the body fluid sample on the upper surface of the film while the pressure member remains in contact with the skin of the user.

10. A method of obtaining a body fluid sample for determining the concentration of an analyte in the body fluid sample, the method comprising the acts of:
applying pressure to skin of a user with a pressure member, the pressure member including a skin-contacting area, the skin-contacting area forming an aperture therethrough in which the body fluid sample is collected;
applying a film to the skin with the skin-contacting area, the film including a mediation material;
directing electromagnetic radiation onto at least a portion of the film to cause the mediation material to convert the radiation to thermal energy which forms an aperture in the film and assists in creating a tear in the skin; and
stretching the skin by use of the applied pressure member, the stretching creating the tear in the skin such that the applied pressure causes the body fluid sample to flow from the tear.

11. The method of claim 10, further comprising collecting the body fluid sample flowing from the tear.

12. The method of claim 10, wherein the film comprises at least a gelatin layer that includes the mediation material.

13. The method of claim 12, wherein the film is a multilayer film, the multilayer film comprising a collection layer and the gelatin layer, the collection layer and the gelatin layer being adjacent to each other.

14. The method of claim 13, wherein the multilayer film further comprises a support layer, the gelatin layer being located between the collection layer and the support layer.

15. The method of claim 10, wherein the pressure member further includes a body and the film, the body including the skin-contacting area.

16. The method of claim 15, wherein the body further includes a sidewall encompassing and extending from the skin-contacting area of the body, the sidewall including an exterior surface, the skin-contacting area being configured to receive the film such that the film completely covers the aperture formed in the skin-contacting area.

17. The method of claim 16, wherein the film is detachably connected to the skin-contacting area.

18. The method of claim 16, wherein the sidewall is a conical-shaped cup.

19. A method of obtaining a body fluid sample for determining the concentration of an analyte in the body fluid sample, the method comprising the acts of:
applying pressure to skin of a user with a pressure member, the pressure member including a film, the film comprising a gelatin layer having high electromagnetic energy absorbent particles suspended therein, the high electromagnetic energy absorbent particles being configured to produce heat when excited by high electromagnetic energy;
transferring the produced heat to the skin of the user at a site of the applied pressure, which softens the skin of the user at the site; and
stretching the skin by use of the applied pressure member, the stretching creating a tear in the skin such that the applied pressure causes the body fluid sample to flow from the tear.

20. The method of claim 19, further comprising collecting the body fluid sample flowing from the tear.

21. The method of claim 19, wherein the gelatin layer further includes a patterned coating of reflective material.

22. A method of obtaining a body fluid sample for determining the concentration of an analyte in the body fluid sample, the method comprising the acts of:
applying pressure to skin of a user with a pressure member, the pressure member including a body and a film, the body having a sidewall encompassing and extending from a top portion of the body, the top portion forming a recess that receives an insert, the insert having an aperture therein;
directing electromagnetic radiation onto at least a portion of the film to heat the skin of the user at a site of the pressure, which softens the skin of the user at the site of the pressure;
stretching the skin by use of the applied pressure member, the stretching creating a tear in the skin such that the applied pressure causes the body fluid sample to flow from the tear; and
collecting the body fluid sample flowing from the tear.

23. The method of claim 22, wherein the aperture is a narrowing aperture.

24. The method of claim 22, wherein the aperture defines an interior surface that maintains a seal with the skin of the user in response to the applying.

25. The method of claim 24, wherein the interior surface forms a conically shaped aperture prior to and during the act of applying pressure.

26. A method of obtaining a body fluid sample for determining the concentration of an analyte in the body fluid sample, the method comprising the acts of:

applying pressure to skin of a user with a pressure member, the pressure member including a film, the film comprising at least a gelatin layer having high electromagnetic energy absorbent particles suspended therein, the high electromagnetic energy absorbent particles being dye particles or carbon black;

heating the skin at the site of the pressure to soften the skin;

stretching the skin by use of the applied pressure member, the stretching creating a tear in the skin such that the applied pressure causes the body fluid sample to flow from the tear; and collecting the body fluid sample flowing from the tear.

* * * * *

UNITED STATES PATENT AND TRADEMARK OFFICE
CERTIFICATE OF CORRECTION

PATENT NO. : 7,896,819 B2  
APPLICATION NO. : 11/665118  
DATED : March 1, 2011  
INVENTOR(S) : Mihailo V. Rebec et al.

Page 1 of 1

It is certified that error appears in the above-identified patent and that said Letters Patent is hereby corrected as shown below:

On the title page, item (54) and col. 1, line 3, replace "SYSTEM IN THEREFOR" with --SYSTEM THEREFOR--.

Col. 15, line 1, in Claim 6, replace "Claim 4" with --Claim 5--.

Signed and Sealed this  
Fourteenth Day of June, 2011

David J. Kappos  
*Director of the United States Patent and Trademark Office*